US008168140B2

(12) United States Patent
Beerling et al.

(10) Patent No.: US 8,168,140 B2
(45) Date of Patent: May 1, 2012

(54) MICROFLUIDIC APPARATUSES WITH NANOCHANNELS

(75) Inventors: Timothy Beerling, San Francisco, CA (US); Karsten G. Kraiczek, Waldbronn (DE); Reid A. Brennen, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 978 days.

(21) Appl. No.: 11/669,682

(22) Filed: Jan. 31, 2007

(65) Prior Publication Data
US 2008/0180188 A1    Jul. 31, 2008

(51) Int. Cl.
B01L 3/00   (2006.01)
B01L 3/18   (2006.01)
G01N 1/10   (2006.01)

(52) U.S. Cl. ........ 422/503; 422/500; 422/501; 422/502; 422/504; 436/180

(58) Field of Classification Search ............... 422/100, 422/500–504; 436/180
See application file for complete search history.

(56) References Cited

U.S. PATENT DOCUMENTS

| | | | |
|---|---|---|---|
| 4,943,032 A | | 7/1990 | Zdeblick |
| 6,379,929 B1* | | 4/2002 | Burns et al. ............... 435/91.2 |
| 2002/0045272 A1* | | 4/2002 | McDevitt et al. ............ 436/518 |
| 2004/0052657 A1* | | 3/2004 | Van Lintel et al. ........... 417/322 |
| 2004/0255643 A1 | | 12/2004 | Wise et al. |
| 2006/0001039 A1 | | 1/2006 | Zamanian |

FOREIGN PATENT DOCUMENTS

| | | |
|---|---|---|
| EP | 1279639 A2 | 1/2003 |
| JP | 2006184010 A | 7/2006 |
| WO | 9700442 A1 | 1/1997 |

OTHER PUBLICATIONS

Search Report dated May 4, 2008 in UK Application No. 0800269.3, filed Jan. 8, 2008.
Abgrall, P. et al., Lab-on-chip technologies: making a microfluidic network and coupling it into a complete microsystem—a review, J. Micromech. Microeng., 2007, R15-R49, vol. 17.
Choi, Chang-Hwan et al., Apparent slip flows in hydrophilic and hydrophobic microchannels, Physics of Fluids, Oct. 2003, pp. 2897-2902, vol. 15, No. 10.
Jang, Won Ick, et al., Fabrication of MEMS devices by using anhydrous HF gas-phase etching with alcoholic vapor, J. Micromech. Micromeng., 2002, pp. 297-306, vol. 12.

(Continued)

*Primary Examiner* — Jill Warden
*Assistant Examiner* — Dean Kwak (57) ABSTRACT

In some embodiments of the present invention, the buried silicon oxide technology is employed in the fabrication of fluid channels, particularly nanochannels. For example, a fluid channel can be made in a buried silicon oxide layer by etching the buried oxide layer with a method that selectively removes silicon oxide but not silicon. Thus, one dimension of the resulting fluid channel is limited by the thickness of the buried oxide layer. It is possible to manufacture a very thin buried oxide layer with great precision, thus a nanochannel can be fabricated in a controlled manner. Moreover, in addition to buried oxide, any pairs of substances with a high etch ratio with respect to each other can be used in the same way. Further provided are the fluid channels, apparatuses, devices and systems comprising the fluid channels, and uses thereof.

6 Claims, 7 Drawing Sheets

OTHER PUBLICATIONS

Lee, Choonsup et al., A Nanochannel Fabrication Technique without Nanolithography, Nano Letters, 2003, pp. 1339-1340, vol. 3, No. 10.

Gravesen P., et al, Microfluidics—a review, J. Micromech. Microeng vol. 3, 1997, pp. 168-182.

Sharma S., et al, Silicon-on-Insulator Microfluidic Device With Monolithic Sensor Integration for LTAS Applications, Journal of Microelectromechanical Systems, Vol. 15, No. 2, Apr. 2006, pp. 309-313.

* cited by examiner

MICROFLUIDIC APPARATUSES WITH NANOCHANNELS

BACKGROUND OF THE INVENTION

In the push for better resolution for HPLC (high performance liquid chromatography), the reduction of bead size has been shown to be very effective. At a given pressure, the reduction in bead size will reduce the flow rate, but increase the fluidic impedance of the separation column: for a given pressure, a 2× reduction in average bead diameter will reduce the flow rate by a factor of 4×. While high flow rates are still often desirable, low flow rates are of increasing interest, particularly in the field of proteomics, where sample injection volumes may be quite low and where LC-MS (liquid chromatography-mass spectrometry) flow rates can result in greater mass spectrometer sensitivity.

In systems where nanoflows (flows less than 1 microliter/minute) are required with high applied pressures, the fluidic path will have a high impedance to flow. Narrow channels, such as those with at least one cross-sectional dimension less than one micron (nanochannels), may be required for these very low flows, particularly if these channels are employed in flow control for the HPLC system. However, controlling channel sizes at these submicron dimensions is challenging. For isotropic etching, both channel width and depth can be difficult to control. Therefore, an improved method of fabricating nanochannels is desirable.

BRIEF DESCRIPTION OF THE DRAWINGS

FIG. 2. Fabrication of nanochannels through vias. Once vias are created, the buried oxide can be etched, for example, with HF. Eventually the individual etch fronts coalesce, forming a continuous channel. Increasing the etch time will increase the channel width.

FIG. 5 shows a portion of a microfluidic apparatus having a back-filled trench. 102 and 106 are silicon layers, and 104 is a buried silicon oxide layer. A trench 502 is made in 102 by etching silicon but not silicon oxide. The silicon oxide in the part of 104 under the trench 502 is then etched, and the entire, extended trench is back-filled with silicon (hatched area), creating a break in the buried silicon oxide layer. Vias 108 are made in silicon layer 102, and the buried oxide layer can be accessed through the vias to form a channel as described in FIG. 1A, FIG. 1B, FIG. 4 and the disclosure.

FIG. 6. Top View of a high impedance microfluidic channel, with the solid lines representing the perimeter of the channel. The channel height is 2000 Angstroms. The fluid input and output ports are shown, but the structure is symmetric, and the ports can be reversed. With 20 bar applied across the two ports, the region of grey represents areas with fluid velocity magnitudes greater than 0.025 m/sec, measured 1000 Angstroms above the channel bottom. There are two stagnant regions where flow is below this value. Maximum velocity in the channel is about 1.0 m/sec. Modeling performed with CFD-ACE.

DESCRIPTION OF THE INVENTION

In some embodiments of the present invention, the buried silicon oxide technology is employed in the fabrication of fluid channels, particularly nanochannels. For example, a fluid channel can be made in a buried silicon oxide layer by etching the buried oxide layer with a method that selectively removes silicon oxide but not silicon. Thus, one dimension of the resulting fluid channel is limited by the thickness of the buried oxide layer. It is possible to manufacture a very thin buried oxide layer with great precision, thus a nanochannel can be fabricated in a controlled manner. Moreover, in addition to silicon and silicon oxide, any pairs of substances with a high etch ratio with respect to each other can be used in the same way. Further provided are the fluid channels, apparatuses, devices and systems comprising the fluid channels, and uses thereof.

Prior to describing the invention in further detail, the terms used in this application are defined as follows unless otherwise indicated.

DEFINITION

A "microfluidic apparatus" is an apparatus with a fluidic circuit suitable for the manipulation of microliter or nanoliter volumes of fluids.

A "fluidic circuit" is a channel or combination of channels that allows fluid to enter and exit.

A "buried oxide layer" is a silicon oxide layer next to a silicon layer. In some cases, the silicon oxide layer is sandwiched between two silicon layers.

The "dimension" of a fluid channel means the smallest dimension of the cross-section of the fluid channel.

Construction of Nanochannels

Figure 1A:
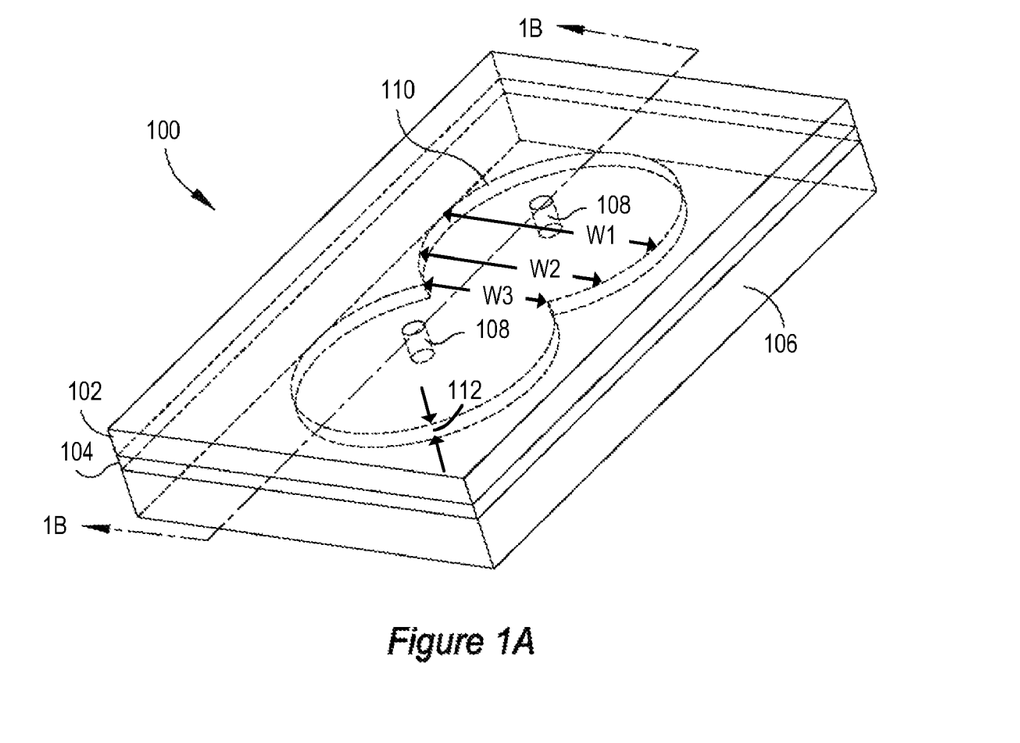
FIG. 1A. Isometric view of a buried oxide silicon wafer comprising a fluid channel in the buried oxide layer. The wafer 100 comprises an active layer 102, a handle layer 106, and a buried oxide layer 104 in between. Vias 108 are formed in the active layer by an etching technology that removes silicon but not silicon oxide. A fluid channel 110 is fabricated in the buried oxide layer 104 by an etching technology that removes silicon oxide but not silicon.
Figure 1B:
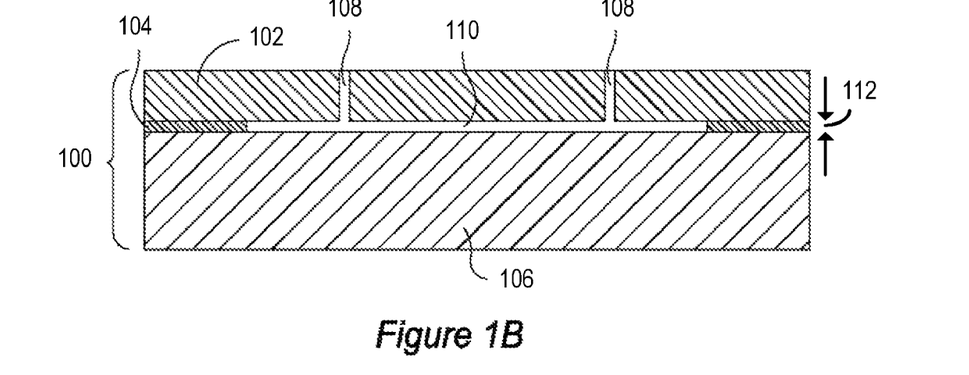
FIG. 1B. Cross-section view of the buried oxide silicon wafer shown in FIG. 1A.

FIG. 1A provides an isometric view of a microfluidic apparatus comprising a nanochannel prepared according to certain embodiments of the present invention, and FIG. 1B is a schematic diagram illustrating a cross-section of the microfluidic apparatus shown in FIG. 1A. In these "sandwich" embodiments, a nanochannel is formed in a silicon wafer 100 with a buried oxide layer 104, which is sandwiched between an active layer 102 and a handle layer 106. The handle, oxide and active layers can be bonded together by a high temperature process. Alternatively, the oxide layer can be generated by oxygen implantation in a bulk silicon wafer, and a subsequent annealing step. Buried oxide silicon wafers are commonly used in the semiconductor industry (see, e.g., Colinge, 1988;

Horsley et al., 2003). The active layer can be, for example, a few microns deep to hundreds of microns deep, and the oxide layer may be generally 0.05 to 10 microns in thickness (see, e.g., thickness 112). The oxide thickness can be easily controlled to +/−5%, even for the 0.05 micron oxide thickness (500 Angstroms), and such material is commercially available.

Figure 2:
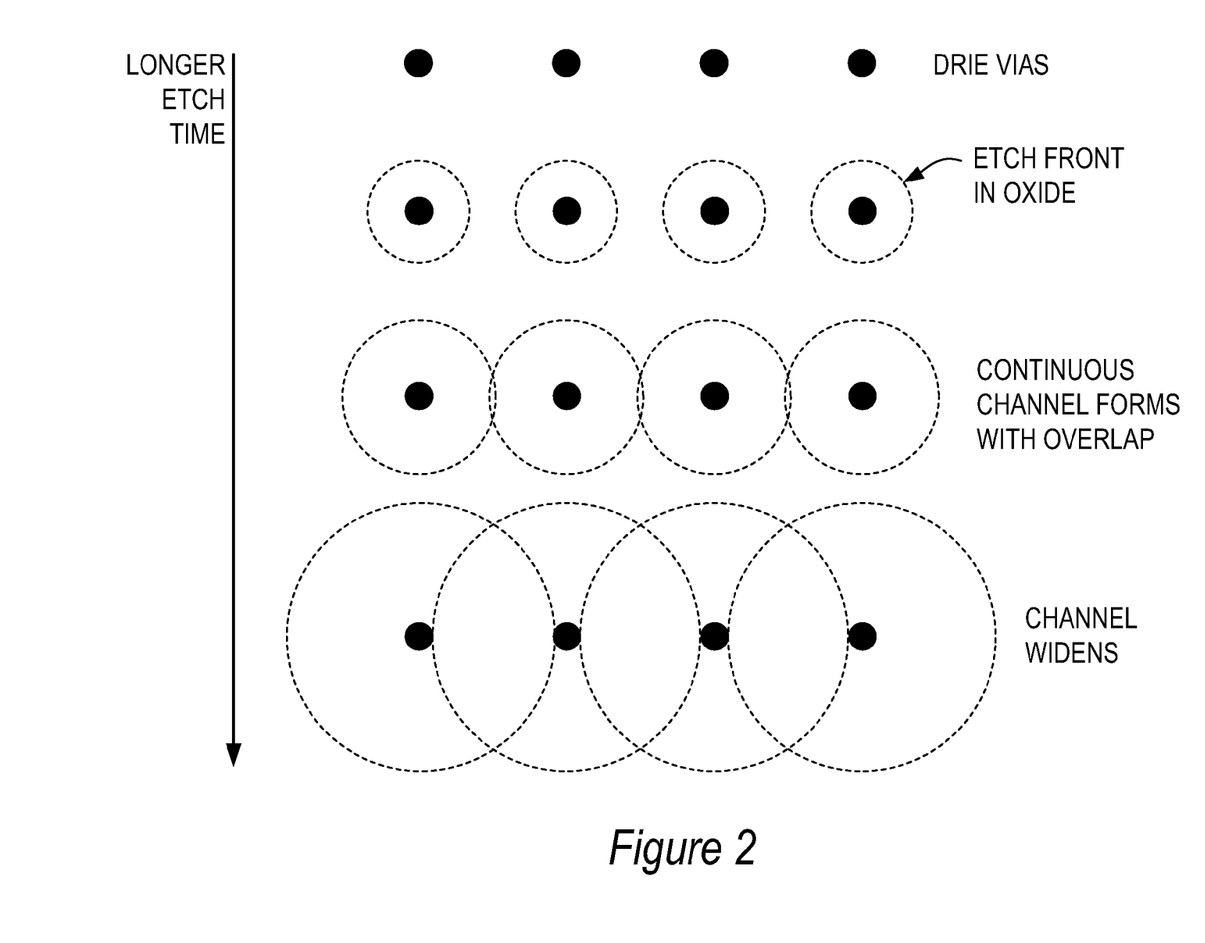
Figure 3:
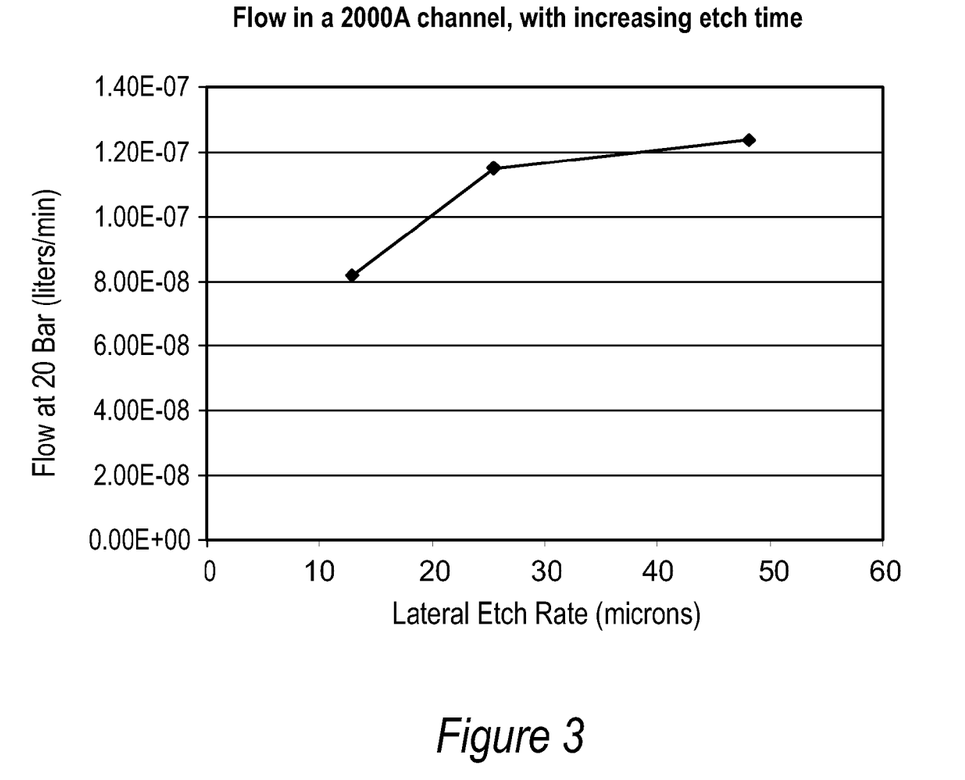
FIG. 3 shows the change in flow rate at 20 Bar with increasing overetch in the buried oxide layer of FIGS. 1 and 2. The channel height is 2000 Angstroms. The modeling was performed with the software CFD-ACE.

To create a channel with sub-micron dimensions, the buried oxide is selectively removed. The oxide can be removed with, for example, the HF:DI wet etch chemistry. The HF:DI wet etch technique is known in the art. Briefly, a mixture of hydrofluoric acid and deionized water is used to etch silicon oxide. The mixture does not attack silicon. In this example, to etch the buried oxide it is accessed through the active layer. This can be done with deep reactive ion etching (DRIE) of silicon, creating high aspect ratio vias 108 and using the buried oxide as an etch stop. This technique has been previously described (Horsley et al., 2003). Once vias are created, the buried oxide 104 can be etched with HF through the vias. Eventually the individual etch fronts overlap and coalesce, forming a continuous channel having a varying width (see, e.g., the widths W1, W2 and W3 in FIG. 1A, and the process flow shown in FIG. 2). One dimension of this channel 110 is limited by the thickness 112 of the oxide layer since HF:DI does not attack the silicon above or below the oxide layer. If the oxide thickness 112 is very small with respect to the lateral etch of the channel (defined by the varying widths W1, W2 and W3), overetching will have minor impact on fluidic impedance. FIG. 3 shows the effect of etch time on flow rate. At the point when the etch fronts in the oxide first overlap and coalesce to form a continuous channel, the flow rate is rather sensitive to etch time. However, as the etch time becomes much longer, the effect on the flow rate becomes less pronounced. In the example shown in FIG. 3, a linear fit for the two data points at longer etch times gives a flow rate change of 0.4 nanoliters/minute for every extra micron of etching, which is quite insensitive. Since etch control of a few microns can be achieved by standard micromachining techniques, the nanochannel can be fabricated in a well-controlled manner.

Figure 4:
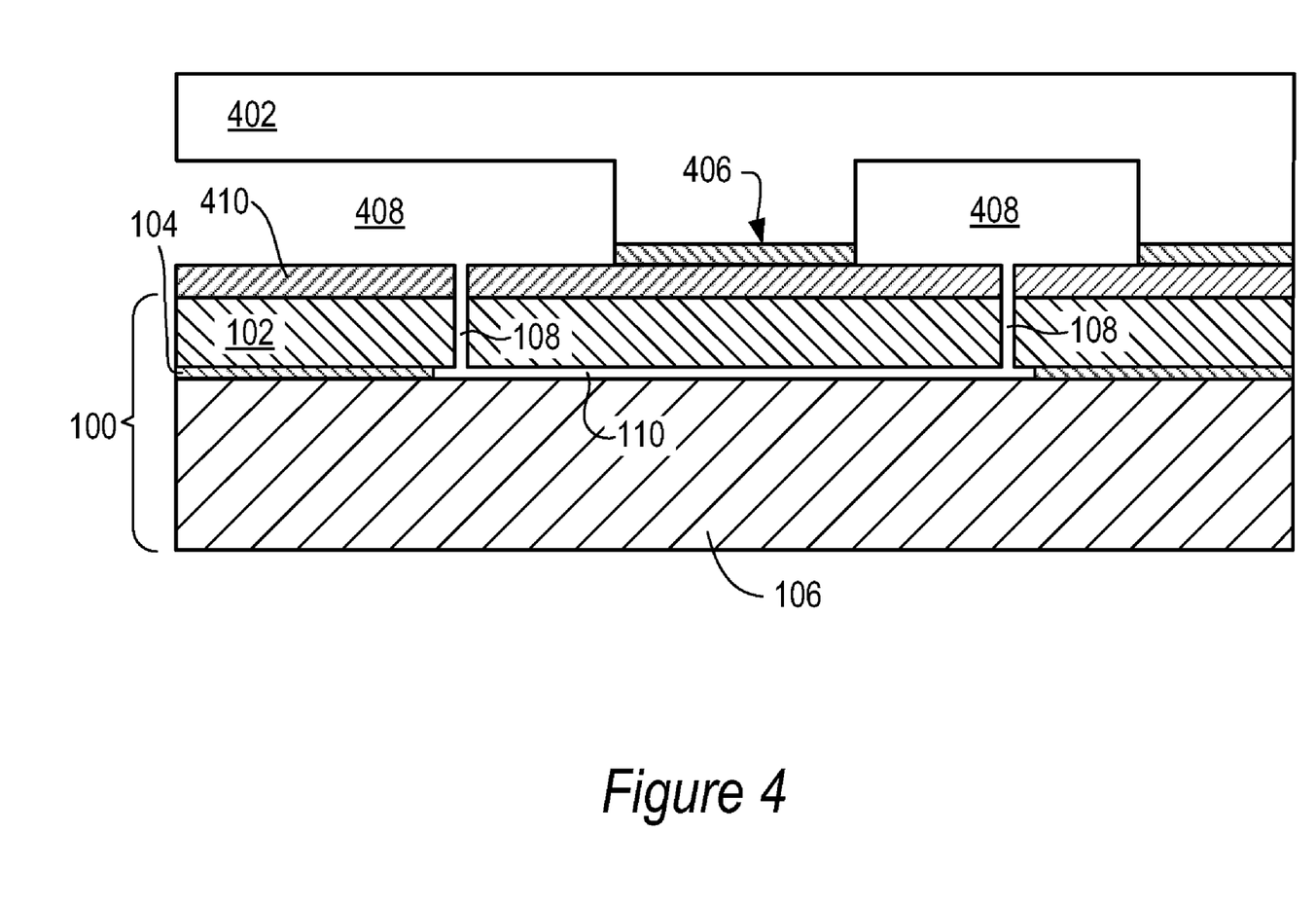
FIG. 4. Exemplary cross-section of a two layer microfluidic apparatus, with a narrow channel (nanochannel) 110 formed by the removal of a buried oxide. The wider channel (microchannel) 408 can be formed by wet or dry micromachining, and is not held to the same flow control tolerance as the narrow channel.

In some embodiments of the present invention, the microfluidic apparatus comprises at least one larger channel, such as a microchannel. FIG. 4 is a schematic diagram of the cross-sectional view of a portion of a microfluidic apparatus comprising a microchannel. Two bonded substrates 402 and 100 are employed in this example. These two substrates may be any substrates that can be bonded together, such as glass and silicon or silicon and silicon. The two substrates are bonded by a bonding layer 406. Bonding can be achieved by any method known in the art, such as anodic, fusion, or thermocompression bonding. There may also be a dielectric layer 410 between the first and second substrates for photomasking purposes. A microchannel 408 is formed by etching the top substrate 402. This channel is typically larger than one micron and of lower dimensional control requirement, since this channel will have a minimal pressure drop per unit length compared to a high-impedance channel (nanochannel). Both dry and wet etching techniques can be used to fabricate this top channel. A nanochannel can be formed in the bottom substrate, which is a buried oxide silicon wafer, as described above.

Figure 5:
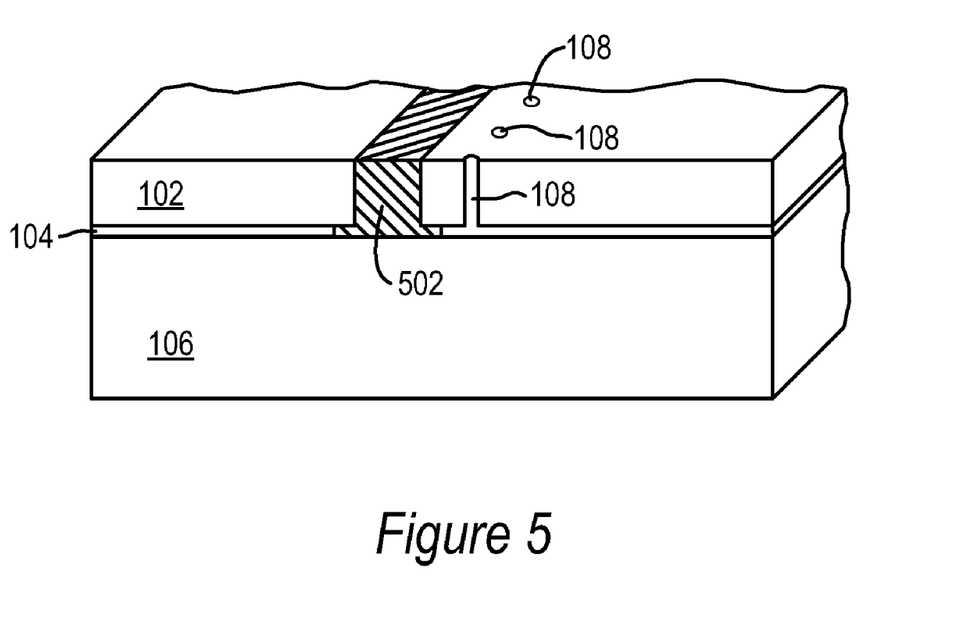

Other construction strategies according to methods established in the art can also be used. For example, DRIE trenches can be formed that create the perimeter of the nanochannel (FIG. 5). The trench 502 in FIG. 5 is formed in the active layer silicon 102, and after DRIE, a short HF dip removes the silicon dioxide only in the region near the bottom of the trench. The trench is then backfilled with polysilicon. This effectively creates a break in the oxide along the bottom of the trench. If a DRIE via 108 is created near the trench, an HF release step will terminate at the perimeter defined by the polysilicon backfilled trench.

In the examples above, silicon and silicon oxide are used in the bottom substrate. The availability of etching techniques that selectively remove silicon but not silicon oxide, and vice versa, renders it possible to control the extent of etching in the fabrication of nanochannels in the "sandwich" embodiments. Therefore, silicon and silicon oxide can be switched, with silicon oxide in the active layer 102 and the handle layer 106, and silicon in 104. The silicon oxide and silicon portions are then etched with etching methods selective for silicon oxide and silicon, respectively. Furthermore, other pairs of substances with similar properties can be employed as well to form the "sandwich" structure, the middle of which is the substance that defines the channel thickness. The pair of substances for 102 and 104 should have a high etch ratio with respect to each other, namely for a given etching method, the etch rate in one substance is negligible when compared to the etch rate in the other. Suitable pairs of substances include, without being limited to, silicon and silicon oxide, silicon and aluminum, silicon and titanium, and silicon and titanium/tungsten alloy.

Accordingly, some embodiments of the present invention provide a microfluidic apparatus comprising a nanochannel in a first portion of the microfluidic apparatus, wherein said first portion is made of a first substance and is next to a second portion made of a second substance, wherein the first and second substances have a high etch ratio with respect to each other. In some preferred embodiments, the first substance is silicon oxide and the second substance is silicon. In some other preferred embodiments, the first substance is silicon and the second substance is silicon oxide. When the first substance is silicon, the second substance may also be selected from the group consisting of, for example, aluminum, titanium, tungsten, and titanium/tungsten alloy. Conversely, when the second substance is silicon, the first substance may be selected from the group consisting of, for example, aluminum, titanium, tungsten, and titanium/tungsten alloy.

"Non-sandwich" fabrication methods can also be employed. For example, the nanochannels can be formed by the removal of oxide in the oxide layer 104 before bonding of the oxide layer 104 with the silicon layer 102. Thus, the oxide is selectively removed by standard photolithographic and etching techniques, the wafers are bonded, and the active layer is lapped and polished to the desired depth. One then only needs to etch DRIE vias in the active layer to complete the processing if vias are desired, e.g., between microchannels and nanochannels. No additional HF step is required. In these embodiments, the oxide layer does not need to be sandwiched between two silicon layers, because no silicon layer is required to serve as an etch stop. Compared to the "sandwich" fabrication methods described above, this technique offers a larger variety of channel shapes and routing possibilities between vias. Also, with this technique, an oxide that might be needed to cover the nanochannel (for chemical reasons) can be created by a second oxidation step after etching on the handle wafer. The overall tolerance of the channel height would, of course, increase by approximately a factor of two. A possible oxide layer on the backside of the active layer may also be employed, but would not add or decrease from the channel height. Furthermore, in these embodiments, any material can generally be used as long as each layer can be manufactured individually, and different layers can be successfully bonded together.

The nanochannel generally has a dimension of one micron or less. For example, its dimension may be about 1, 0.9, 0.8, 0.7, 0.6, 0.5, 0.4, 0.3, 0.2, or 0.1 micron or less. In some embodiments, the dimension is about 0.09, 0.08, 0.07, 0.06, 0.05, 0.04, 0.03, 0.02, or 0.01 micron or less. The flow rate in the nanochannel may be, for example, in the range of a few microliters to a few nanoliters per minute, such as about 50, 30, 10, 9, 8, 7, 6, 5, 4, 3, 2, 1 microliters per minute, or 800, 600, 400, 200, 150, 100, 80, 60, 40, 20, 10, 9, 8, 7, 6, 5, 4, 3, 2 or 1 nanoliter per minute.

In addition to the nanochannel, the microfluidic apparatus may optionally comprise a microchannel in its fluidic circuit. In some embodiments, the microchannel is located in the second portion, which is made of the second substance. The microchannel generally has a dimension of at least one micron. The dimension of a microchannel is typically about 5, 10, 20, 40, 60, 80, 100, 200, 300, 400, 500 microns or more.

The present invention also provides a device comprising the microfluidic apparatus described herein. The microfluidic apparatus or device may be part of a system. Exemplary systems include, without being limited to, systems for DNA sequencing, microarray analysis, enzymatic reactions, chemical reactions, flow cytometry, fluorescence measurement, UV absorption measurement, liquid chromatography, and/or liquid chromatography/mass spectrometry. Thus, the system may comprise, for example, an LC column, a mass spectrometer, a monitor, a data recorder, a microarray holder, a reaction chamber, a cell sorter, a fluorospectrometer, and/or a fluorometer. The nanochannel may be part of, or connected (directly or indirectly) to, any of these exemplary devices or to other devices not listed above.

Another aspect of the present invention provides a method for fabricating a microfluidic apparatus. The method comprises etching a first substance to form a nanochannel of the present invention, wherein the first substance is next to a second substance, and the first and second substances have a high etch ratio with respect to each other, thus each substance can serve as an etching stop for the other. In some embodiments, multiple vias are first etched in the second substance, said vias being ended at the border of the first and second substances, then the second substance is etched through the vias.

Yet another aspect of the present invention provides a method for controlling fluid flow rate in a microfluidic apparatus, comprising a nanochannel of the present invention in the microfluidic apparatus.

Figure 6:
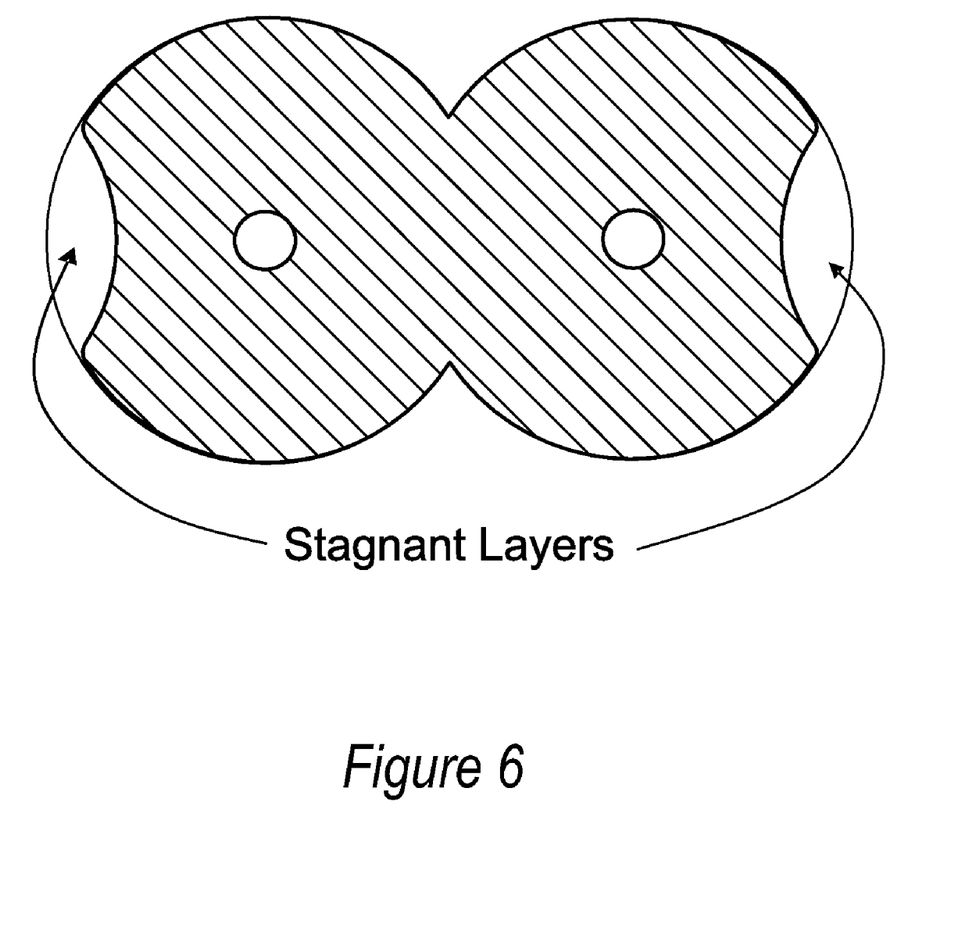

The channels in the microfluidic apparatuses can be designed according to knowledge in the art. For example, if two vias are used to create a channel as in FIG. 4, a stagnant region may be formed in the nanochannel. FIG. 6 shows a top View of a high impedance microfluidic channel, with the solid lines representing the perimeter of the channel. The channel thickness is 2000 Angstroms. With 20 bar applied across the two ports, the region of grey represents areas with fluid velocity magnitudes greater than 0.025 m/sec, measured 1000 Angstroms above the floor. There are two stagnant regions where flow is below this value.

Figure 7:
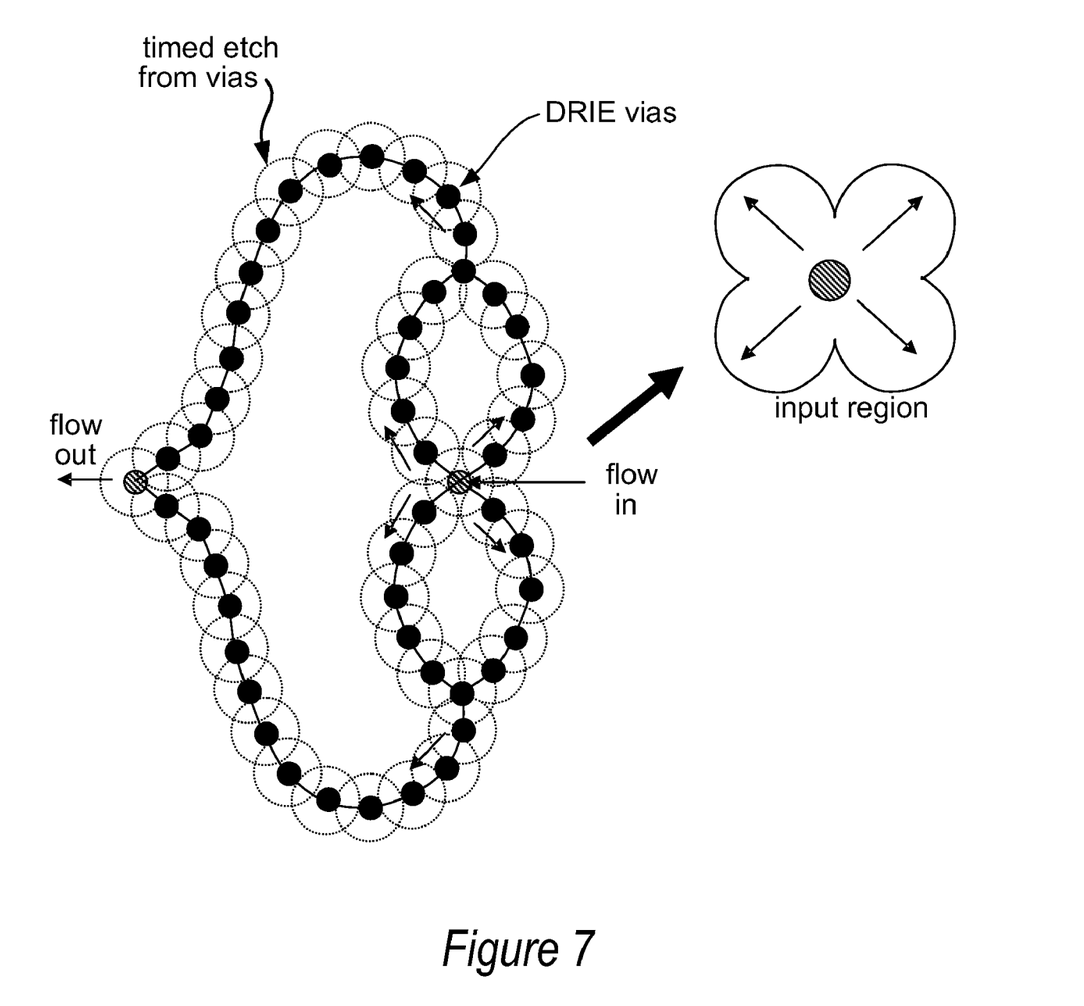
FIG. 7. An example design that will reduce the stagnation areas in the input region of the channel (see FIG. 6). This configuration will allow all the fluid entering the input port to exit the input region at the same time. By locating the vias in the appropriate places and setting the etch timing optimally, the input region will completely empty continuously. Note that the exit region will have an area of stagnation on the left side of the etch front.

The channels are not limited to single paths between two ports; this is one possible way to deal with fluid stagnancy. Multiple channels can be created in a variety of configurations. For example, FIG. 7 shows a design to reduce the amount of stagnation in an input port. This configuration will allow all the fluid entering the input port to exit the input region, without the formation of a stagnant layer. By locating the vias in the appropriate places and setting the etch timing optimally, the input region will not have excessive stagnation. Many other different configurations may be possible. Further, the etch vias do not necessarily need to be circular but may have other shapes. With more than one via, an alternating back and forth between the microchannels and nanochannels can be constructed, such that there is reasonable flow in every via. With the serial combination of impedances, there is a high overall impedance. It might also be possible to plug all the vias, except for a single input and exit via. These vias may be plugged by thin film deposition process that plugs the via, but does not totally block a given nanochannel.

Thus, some embodiments of the present invention provide a microfluidic apparatus that comprises at least one buried silicon oxide portion, wherein the buried silicon oxide portion comprises at least one fluidic channel. The buried oxide portion may be sandwiched between two silicon portions. The fluidic channel may be, for example, a microchannel or nanochannel, such as a channel with a dimension of 0.5 micron or less, 0.1 micron or less, or 0.01 micron or less. Systems comprising such a microfluidic apparatus are also provided. Exemplary systems include, without being limited to, a system comprising a liquid chromatography column, mass spectrometer, or UV detection cell.

The present invention also provides methods of manufacturing such microfluidic apparatuses and systems. Some embodiments provide a method for manufacturing a microfluidic apparatus, comprising providing a silicon oxide layer between two silicon layers, and etching a fluidic channel in the silicon oxide layer with at least one of the silicon layers as an etching stop. The etching may be performed by any method known in the art. For example, the fluidic channel can be prepared by etching the silicon oxide with a HF:DI mixture. In some embodiments, the fluidic channel is prepared by first etching vias in one of the silicon layers, said vias being ended at the silicon oxide layer, and etching the silicon oxide layer through the vias.

Another aspect of the present invention provides a method for controlling fluid flow in a microfluidic apparatus, comprising including a nanochannel in the apparatus, wherein the nanochannel is located in a portion of the apparatus made of a first substance, said portion is next to a second portion made of a second substance, and the first substance and the second substance have a high etch ratio with respect to each other. In some embodiments, the first substance is sandwiched between two layers of the second substances. In some embodiments, the first substance is silicon oxide and the second substance is silicon. In some other embodiments, the first substance is silicon and the second substance is silicon oxide. In some further embodiments, the first substance is selected from the group consisting of titanium, tungsten, aluminum, and titanium/tungsten alloy, and the second substance is silicon. Conversely, in some other embodiments, the first substance is silicon, and the second substance is selected from the group consisting of titanium, tungsten, aluminum, and titanium/tungsten alloy.

While this invention is particularly shown and described with references to exemplary embodiments thereof, it will be understood by those skilled in the art that various changes in form and details may be made therein without departing from the spirit of the invention described in this disclosure.

ABBREVIATIONS

In this disclosure, the following abbreviations have the following meanings. Abbreviations not defined have their generally accepted meanings.

° C.=degree Celsius hr=hour min=minute sec=second
M=molar
mM=millimolar
μ=micromolar
nM=nanomolar
ml=milliliter
μl=microliter
nl=nanoliter
mg=milligram
μg=microgram
HPLC=high performance liquid chromatography
LC=liquid chromatography
MS=mass spectrometry
HF=hydrogen floride
DI=deionized water

REFERENCES

Colinge, J. P., "Thin-film SOI devices: A perspective," Microelectronic Engineering, v. 8, n 3-4, pages 127-47 (December 1988).

Horsley, D. A.; Daneman, M. J.; Hart, M. R.; Hogan, K.; Beerling, T.; Behin, B.; Kiang, M. H. "High performance MEMS-based 8*8-port optical switch," CLEO/Pacific Rim 2003. The 5th Pacific Rim Conference on Lasers and Electro-Optics, part 1, page 99, v. 1 (2003).

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

The invention claimed is:

1. A microfluidic apparatus, comprising:
    first and second silicon portions, the first silicon portion having first and second ports; and
    a buried silicon oxide portion sandwiched between the two silicon portions;
    wherein the buried silicon oxide portion comprises at least one fluidic channel, wherein one of the fluidic channels extends between the first port and the second port and has i) a thickness defined by the first silicon portion and the second silicon portion, and ii) a varying width, the width at least partly defined by overlapping and coalesced etch fronts formed during etching of the one of the fluidic channels through the first and second ports.

2. The apparatus of claim 1, wherein a smallest dimension of a cross-section of the fluidic channel is 0.5 micron or less.

3. The apparatus of claim 1, wherein a smallest dimension of a cross-section of the fluidic channel is 0.1 micron or less.

4. A system comprising the microfluidic apparatus of claim 1.

5. The system of claim 4, further comprising at least one liquid chromatographic column, the fluidic channel connected to the at least one liquid chromatographic column to control fluid flow in the at least one liquid chromatographic column.

6. The system of claim 4, further comprising a mass spectrometer or UV detection cell, the fluidic channel connected to the mass spectrometer or UV detection cell to control fluid flow toward the mass spectrometer or UV detection cell.

* * * * *